US011648300B1

(12) United States Patent
Ivachtchenko et al.

(10) Patent No.: US 11,648,300 B1
(45) Date of Patent: May 16, 2023

(54) PHARMACEUTICAL COMBINATION THERAPY AND PREVENTION WITH APROTININ + NIRMATRELVIR OF SARS-COV-2 AND/OR DISEASE ASSOCIATED WITH THIS INFECTION, INCLUDING COVID-19

(71) Applicants: ASAVI LLC, Hallandale, FL (US); Alexandre Vasilievich Ivachtchenko, Hallandale, FL (US); Alena Alexandrovna Ivachtchenko, Hallandale, FL (US); Nikolay Filippovich Savchuk, Rancho Santa Fe, CA (US)

(72) Inventors: Alexandre Vasilievich Ivachtchenko, Hallandale, FL (US); Andrey Alexandrovich Ivashchenko, Moscow (RU); Alena Alexandrovna Ivachtchenko, Hallandale, FL (US); Ilya Andreevich Ivachtchenko, Moscow region (RU); Nikolay Filippovich Savchuk, Rancho Santa Fe, CA (US)

(73) Assignees: ASAVI LLC, Hallandale, FL (US); Alexandre Vasilievich Ivachtchenko, Hallandale, FL (US); Alena Alexandrovna Ivachtchenko, Hallandale, FL (US); Nikolay Filippovich Savchuk, Rancho Santa Fe, CA (US)

(*) Notice: Subject to any disclaimer, the term of this patent is extended or adjusted under 35 U.S.C. 154(b) by 0 days.

(21) Appl. No.: 17/709,727

(22) Filed: Mar. 31, 2022

(51) Int. Cl.
  *A61K 38/57* (2006.01)
  *A61P 31/14* (2006.01)
  *A61K 31/427* (2006.01)
  *A61K 31/403* (2006.01)

(52) U.S. Cl.
  CPC .......... *A61K 38/57* (2013.01); *A61K 31/403* (2013.01); *A61K 31/427* (2013.01); *A61P 31/14* (2018.01)

(58) Field of Classification Search
  CPC .... A61K 38/57; A61K 31/403; A61K 31/427; A61P 31/14
  See application file for complete search history.

(56) References Cited

U.S. PATENT DOCUMENTS

| | | | |
|---|---|---|---|
| 2022/0177469 A1* | 6/2022 | Klopp | C07D 471/04 |
| 2022/0193235 A1* | 6/2022 | Herzlinger | A61M 5/152 |
| 2022/0193236 A1* | 6/2022 | Herzlinger | A61M 5/002 |
| 2022/0196658 A1* | 6/2022 | Rathe | G01N 33/56983 |
| 2022/0233480 A1* | 7/2022 | Dalsgaard | A61P 31/14 |

FOREIGN PATENT DOCUMENTS

| | | | | |
|---|---|---|---|---|
| WO | WO2021221537 | * | 4/2021 | A61K 38/17 |
| WO | WO2021250648 | * | 12/2021 | C07D 207/267 |
| WO | WO2022039619 | * | 2/2022 | A61K 38/17 |

OTHER PUBLICATIONS

Bojkova et al. Aprotinin Inhibits SARS-CoV-2 Replication. Cells, 9, 2377, pp. 1-13. (Year: 2020).*
Beximco Pharma introduces generic version of Pfizer's Paxlovid for COVID-19 treatment, accessed online Jun. 30, 2022 at https://www.bssnews.net/news/36179 (Year: 2021).*
Bojkova et al. SARS-CoV-2 and SARS-CoV differ in their cell tropism and drug sensitivity profiles. bioRxiv preprint, pp. 1-28. (Year: 2020).*

* cited by examiner

*Primary Examiner* — Marcela M Cordero Garcia
(74) *Attorney, Agent, or Firm* — Paul D. Strain, Esq.; Strain & Strain PLLC

(57) ABSTRACT

The present application relates to the new the pharmaceutical combination therapy and prevention of SARS-CoV-2 and/or disease associated with this infection, including viral and bacterial pneumonia and COVID-19, using aprotinin (APR), ribavirin and/or nirmatrelvir (NIMR), the pharmaceutical kit and the pharmaceutical composition for this pharmaceutical combination therapy and prevention of SARS-CoV-2 and/or disease associated with this infection, including COVID-19.

13 Claims, No Drawings

PHARMACEUTICAL COMBINATION THERAPY AND PREVENTION WITH APROTININ + NIRMATRELVIR OF SARS-COV-2 AND/OR DISEASE ASSOCIATED WITH THIS INFECTION, INCLUDING COVID-19

FIELD OF INVENTION

The present application is directed to a new parenteral antiviral pharmaceutical composition intended for the prevention and treatment of severe acute respiratory syndrome (SARS), as well as diseases caused by SARS, including coronavirus diseases.

BACKGROUND OF THE INVENTION

SARS diseases (e.g., COVID-19) are caused by coronaviruses. The SARS viruses have a tropism for the epithelium of the mucous membranes of the respiratory system. They are characterized by catarrhal damage to the mucous membranes of the larynx, trachea, and bronchi with involvement of the lungs in the process. The infections are transmitted mainly by aerosol transmission.

Severe Acute Respiratory Syndrome Coronavirus 2 (SARS-CoV-2) is RNA virus that causes a 2019 Coronavirus Disease (COVID-19). SARS-CoV-2 is responsible for the ongoing COVID-19 pandemic. SARS-CoV-2 is a virus that belongs to a type of coronavirus associated with SARS-CoV (Coronaviridae Study Group of the International Committee on Taxonomy of Viruses (April 2020). "The species Severe acute respiratory syndrome—related coronavirus: classifying 2019-nCoV and naming it SARS-CoV-2". *Nat. Microbiol.* 2020, 5(4), 536-544. doi:10.1038/s41564-020-0695-z). This virus was first identified in December 2019 in Wuhan city, Hubei province, China. On Mar. 11, 2020, WHO declared the outbreak a public health emergency of international concern. SARS-CoV-2 is the successor to the SARS-CoV-1 virus that caused the SARS outbreak in 2002-2004 ("New coronavirus stable for hours on surfaces". National Institutes of Health (NIH). NIH.gov. 17 Mar. 2020. Archived from the original on 23 Mar. 2020. Retrieved 4 May 2020). SARS-CoV-2 has undergone many changes in two years, and each new mutation has been more perfect than the previous one. First discovered in India in December 2020, the Delta mutation is spreading across continents at an alarming rate. Delta penetrates lung cells more easily than the original virus (the virus that circulated in the early stages of the pandemic). In addition, the Delta strain is more effective in combining infected lung cells with uninfected ones. This could contribute to the more severe course of COVID-19. It is currently the predominant variant of SARS-CoV-2 worldwide. Delta is believed to be more than twice as infectious as previous SARS-CoV-2 variants (K. Katella. 5 Things to Know About the Delta Variant. Yale Medicine Nov. 19, 2021. https://www.yalemedicine.org/nMws/5-things-to-know-delta-variant-covid).

The new variant of coronavirus Omicron was detected in laboratories in Botswana and South Africa on 22 Nov. 2021. The variant has an unusually large number of mutations, several of which are novel and a significant number of which affect the spike protein targeted by most COVID-19 vaccines at the time of discovering the Omicron variant. This level of variation has led to concerns regarding its transmissibility, immune system evasion, and vaccine resistance. Omicron spreads faster than any previously known variant.

As of Dec. 17, 2021, 77 countries have now reported cases of Omicron, and "the reality is that Omicron is probably in most countries, even if it hasn't been detected yet (L. Smith-Spark, What can the world learn from countries where Omicron is surging? CNN Fri Dec. 17, 2021. https://www.cnn.com/2021/12/17/health/covid-omicron-what-can-the-world-learn-cmd-intl/index.html).

As of Jan. 28, 2022, 364,191,494 confirmed cases of people infected with coronavirus were registered in the world, of which 5,631,457 unfortunately died (https://www.who.int/emergencies/diseases/novel-coronavirus-2019).

Vaccination remains one of the main public health interventions to combat SARS-CoV-2. However, vaccine development times of at least six months limit their applicability during outbreaks of new strains of SARS-CoV-2, like the Omicron strain. Therefore, the new development of new highly effective anticoronavirus drugs is an urgent task.

Previous attempts to provide an anticoronavirus drug include a nirmatrelvir/ritonavir combination sold under the brand name PAXLOVID (PAX). Nirmatrelvir (BEXOVID, PF-07321332,—hereinafter referred to as "NIMR") inhibits a cysteine residue in the 3C-like protease (3CLPRO) of RNK, viruses including of SARS-CoV-2. Ritonavir slows down NIMR's breakdown to help it remain in the body for a longer period at higher concentrations.

On Dec. 22, 2021, the United States FDA issued an emergency use authorization (EUA) for Pfizer's PAX (NIMR tablets and ritonavir tablets, co-packaged for oral use) for the treatment of mild-to-moderate coronavirus disease (COVID-19) in adults and pediatric patients (12 years of age and older weighing at least 40 kilograms or about 88 pounds) with positive results of direct SARS-CoV-2 testing, and who are at high risk for progression to severe COVID-19, including hospitalization or death. PAX is available by prescription only and should be initiated as soon as possible after diagnosis of COVID-19 and within five days of symptom onset. PAX is administered as three tablets (two tablets of NIMR and one tablet of ritonavir) taken together orally twice daily for five days, for a total of 30 tablets. PAX is not authorized for use for longer than five consecutive days (https://www.fda.gov/news-events/press-announcements/actualizacion-sobre-el-coronavirus-covid-19-la-fda-au-toriza-el-primer-tratamiento-antiviral-oral).

Previous attempts to provide an anticoronavirus drug also include a method of treating of moderate COVID-19 patients by the intravenous aprotinin (APR) and oral AVIFAVIR (favipiravir, FVP) combination therapy. This therapy is more effective because primary and secondary efficacy endpoints of therapy by the APR+FVP combination significantly better than efficacy endpoints of therapy by the individual components (Table 1). (Ivashchenko A. A. et al. Effect of Aprotinin and Avifavir® Combination Therapy for Moderate COVID-19 Patients. *Viruses* 2021, 13, 1253. https://doi.org/10.3390/v13071253.).

TABLE 1

Primary and secondary efficacy endpoints of therapy by the intravenous aprotinin (APR), oral AVIFAVIR (favipiravir, FVP) and their combination.

| Primary and Secondary Efficacy Endpoints | APR + SOC | FVP + SOC) | APR + FVP + SOC |
|---|---|---|---|
| Median time to elimination of SARS-CoV-2 confirmed by RT-PCR, days (IQR) | 7.5 (6-9) | 4.5 (4-9) | 3.5 (3-4) |
| Median time to normalization of CRP concentration (≤10 mg/L) in patient's blood, days (IQR) | 6.0 (6-6) | 14.0 (5.5-14) | 3.5 (3-5) |
| Median time to normalization of D-dimer concentration (<253 ng/mL) in patient's blood, days (IQR) | 4.5 (3-6) | NA | 5.0 (4-5) |
| Median time to normalization of body temperature (<37° C.), days (IQR) | 3.0 (2-3) | 2.0 (1-3) | 1.0 (1-3) |
| Median time to improvement in clinical status by 2 points on the WHO-OSCI, days (IQR) | 11.0 (6-11) | 14.0 (11.5-16) | 5.0 (5-5) |

TERMS USED IN THE DESCRIPTION

The term "drug" (also called medicine, medicament, pharmaceutical composition, or medicinal drug) refers to a drug used to diagnose, cure, treat, or prevent disease and means a substance (or a mixture of substances in the form of a pharmaceutical composition).

The term "oral drug" refers to solutions, powders, tablets, capsules, and pills that are taken by mouth and swallowed.

The term "parenteral drug" refers to drugs that are injected into the body bypassing the gastrointestinal tract. Parenteral drugs are solutions for injection, inhalation, sprays, including for nasal or drip application, and other finished dosage forms, in this case intended for the treatment and prevention of viral infections and diseases caused by them.

The term "parenteral therapies" are administration of drugs is primarily injections (intravenously, into the muscles, under the skin), inhalations and nasally (spray, drops).

The term "pharmaceutical composition" as used herein means a composition comprising at least two active ingredients (substances), namely aprotinin an inhibitor of RNA viruses, and at least one excipient.

The term "parenteral pharmaceutical composition (PPC)" is intended for parenteral administration of drugs into the body of a patient. These are primarily intravenous, inhalation and nasal routes of drug administration.

The term "excipient" as used herein refers to a compound that is used to prepare a pharmaceutical composition and is generally safe, non-toxic, and neither biologically nor otherwise undesirable, and includes excipients that are acceptable to humans and animals. The present application uses primarily excipients selected from the series: water, sodium chloride, L-lysine monohydrate, sodium hydroxide, hydrochloric acid, benzyl alcohol, ethanol, glycerin, dimethyl sulfoxide, peppermint oil, 1,1,1,2-tetrafluoroethane, and some others.

The term "combination therapy" is therapy that uses more than one medication or modality. Typically, the term refers to using multiple therapies to treat a single disease, and often all the therapies are pharmaceutical. "Pharmaceutical" combination therapy may be achieved by prescribing/administering separate drugs, or, where available, dosage forms that contain more than one active ingredient (such as fixed-dose combinations).

The term "therapeutically effective amount" or "dose" as used herein means the amount of medicine needed to reduce the symptoms of a disease in a patient. The dose of medicine will be tailored to the individual requirements in each case. This dose can vary widely depending on numerous factors, such as the severity of the patient's illness, the age and general health of the patient, other drugs with which the patient is being treated, the method and form of administration of medicine, and the experience of the attending physician. Typically, treatment is started with a large initial "loading dose" to rapidly reduce or eliminate the virus and followed by tapering the dose to a level sufficient to prevent an outbreak of infection.

The term "patient" means a mammal including but not limited to humans, cattle, pigs, sheep, chickens, turkeys, buffaloes, llamas, ostriches, dogs, cats, hamsters, and mice, preferably the patient is a human.

The term "active ingredient (substance)" as used herein means aprotinin and an inhibitor of RNA viruses used in a pharmaceutical composition or drug.

SUMMARY OF THE INVENTION

The first aspect of the present application relates to pharmaceutical combination therapy and prevention of SARS-CoV-2 and/or disease associated with this infection, including COVID-19, using aprotinin (APR), ritonavir and/or Nirmatrelvir (BEXOVID, PF-07321332,—hereinafter referred to as "NIMR") and excipients.

Another aspect of the present application is a pharmaceutical kit for a pharmaceutical combination therapy and prevention of SARS-CoV-2 and/or disease associated with this infection, including COVID-19, consisting of: the parenteral drug TRASYLOL®, or GORDOX®, or APROTEX®, or ANTAGOSAN®, or CONTRYCAL®, or TRASKOLAN®, or others parenteral drugs including APR, or aqueous or saline solution containing APR and a drug including ritonavir or aqueous or saline solution containing ritonavir, or its lyophilizate and/or a drug BEXOVID or aqueous or saline solution containing Nirmatrelvir or its lyophilizate.

Another aspect of the present application is a pharmaceutical composition in the form of an aqueous solution (APC) or lyophilizate (PCL) for a pharmaceutical combination therapy and prevention of SARS-CoV-2 and/or disease associated with this infection, including COVID-19, including APR, ritanovir and/or NIMR and excipients.

According to the present application, a preferred anti-SARS-CoV-2/COVID-19 viral pharmaceutical composition is in form of a lyophilizate (PCL) containing APR, NIMR and excipients.

The excipients are selected from the series: water, sodium chloride, L-lysine monohydrate, sodium hydroxide, hydrochloric acid, benzyl alcohol, ethanol, glycerin, dimethyl sulfoxide, peppermint oil, 1,1,1,2-tetrafluoroethane, and others.

APR is a drug with a long history of clinical use since the 1960s and a good safety profile. APR, under the trade names TRASYLOL®, ANTAGOSAN®, CONTRYCAL®, GORDOX®, and others, is used as an intravenous medication given by injection to reduce bleeding during complex surgeries such as heart and liver surgery (https://www.rxlist.com/trasylol-drug.htm#indications; https://yandex.ru/health/pills/product/gordoks-203), as an antiviral drug for the treatment and prevention of viral respiratory diseases (U.S. Pat. No. 5,723,439).

APR is a nonspecific inhibitor of the serine proteases— especially trypsin, chymotrypsin, plasmin, and kallikrein. The inhibition of kallikrein leads to inhibition of factor XIIa formation, inhibition of the intrinsic pathway of coagulation, fibrinolysis, and thrombin generation, and to the attenuation of the pro-inflammatory response (Solun B, Shoenfeld Y. Inhibition of metalloproteinases in therapy for severe lung injury due to COVID-19. Med. Drug. Discov. 2020, 100052; doi: 10.1016/j.medidd.2020.100052).

APR by inhibiting kallikreins, regulates coagulation by affecting factor XII, plasminogen, and PAR-I thrombin receptor. The mechanism by which SARS CoV-2 promotes thrombo-inflammation involves activation of the kallikreins that trigger neutrophilia by the viral capsid proteins, which leads to the formation of neutrophil extracellular networks (NETs) and vascular microthrombus formation (Colling M. E., Kanthi Y. COVID-19-associated coagulopathy: An exploration of mechanisms. Vasc. Med. 2020, 25(5), 471-478. doi:10.1177/1358863X20932640).

The distribution of serine proteases throughout the vasculature and the key role they play in inflammation may explain how aprotinin, as a nonspecific protease inhibitor, can exert such a multi-tiered anti-inflammatory mechanism of action. Its activity ranges from reduced contact activation of platelets and leukocytes, to reduced extravasation and degranulation of leukocytes, reduced systemic cytokine production, reduced endothelial cell activation, reduced vascular permeability, and reduced bronchial epithelial cell activation (Landis R. C. et al. The antithrombotic and anti-inflammatory mechanisms of action of aprotinin. Ann. Thorac. Surg. 2001, 72 (6), 2169-2175. doi: 10.1016/S0003-4975(01)02821-1.).

APR inhibits the entry of SARS-CoV-2 into cells ((a) M. Hoffmann et al. SARS-CoV-2 Cell Entry Depends on ACE2 and TMPRSS2 and Is Blocked by a Clinically Proven Protease Inhibitor. Cell 2020, 181 (2), 271-280. e8. doi: 10.1016/j.cell.2020.02.052; (b) D. Bojkova et al. Aprotinin Inhibitors SARS-CoV-2 Replication. *Cells* 2020, 9 (11), 2377. https://doi.org/10.3390/cells9112377) and can be used for the prevention and treatment of SARS-CoV-2/COVID-19 (RU 2738885).

NIMR (Nirmatrelvir, BEXOVID, PF-07321332) is an antiviral peptidomimetic developed by Pfizer which acts as an orally active 3C-like protease inhibitor of a cysteine residue in the 3C-like protease (3CLPRO) of RNK, viruses including of SARS-CoV-2. NIMR is a covalent inhibitor, binding directly to the catalytic cysteine (Cys145) residue of the cysteine protease enzyme (Pavan M. et al. Supervised Molecular Dynamics (SuMD) Insights into the mechanism of action of SARS-CoV-2 main protease inhibitor PF-07321332. *J. Enzyme Inhib. Med. Chem.* 2021, 36 (1), 1646-1650. doi:10.1080/14756366.2021.1954919).

The inventors of the present application unexpectedly found that the active ingredients (APR and NIMR) included in the new anti-SARS-CoV-2/COVID-19 pharmaceutical composition do not interact with each other during the preparation, short-term storage, and this composition can use as a parenteral drug.

Another aspect of the present application is directed to anti-SARS-CoV-2/COVID-19 viral parenteral drug, which is PPC of certain embodiments of the present application.

The parenteral drug and PPC according to the present application is intended for the prevention and treatment mainly of SARS-CoV-2 and COVID-19.

Another aspect of the present application is directed to the containing a PPC of the present application container.

Another aspect of the present application is directed to an ampoule and a bottle containing an APC of the present application.

Another aspect of the present application is directed to an inhaler (nebulizer) selected from a number of compressor or ultrasonic or electronic mesh inhaler (nebulizer) containing the APC of the present application.

Another aspect of the present application is directed to a pocket or portable inhaler (nebulizer) containing the APC of the present application.

Another aspect of the present application is directed to a container, which is a can for nasal spray containing the APC of the present application.

Another aspect of the present application is directed to a method for the prevention and/or treatment of SARS-CoV-2 infection and/or disease associated with this infection in a patient by a parenteral (intravenous, inhalation, or intranasal) administration to the patient of the APC of the present application in a therapeutically effective amount.

In accordance with the present application, patients are treated by intravenous administration of with the parenteral drug or the APC of the present application in a therapeutically effective amount once or twice a day (as prescribed by a physician, depending on the patient's condition).

In accordance with the present application, prophylaxis of patients is carried out with a therapeutically effective amount of a nasal spray, which is the APC of the present application.

In accordance with the present application, the prophylaxis is carried out using balloons for nasal spray into the nose (into the nasopharynx) and throat 3-6 times a day into each nostril and the throat (about 1 ml per session and about 3-6 ml per day).

In accordance with the present application, the prophylaxis and treatment of patients is carried out by inhalation using ultrasonic nebulizers 3-6 times a day for 5-7 days a therapeutically effective amount of APC according to the present application.

Another aspect of the present application is directed to the use of the APC or the parenteral drug of the present application for the prevention and/or treatment of the RNA viral infection (SARS-CoV-2) and/or disease associated with this infection (COVID-19) by intravenous, or inhalation, or intranasal administration to a patient of the APC or the parenteral drug of the present application in a therapeutically effective amount.

Another aspect of the present application is directed to the use of the APC or the parenteral drug of the present application in a therapeutically effective amount for the prevention and/or treatment of the RNA viral infection (SARS-CoV-2) and/or disease associated with this infection (COVID-19).

The use of the new APC and the new parenteral drug of the present application containing two active ingredients (NIMR and APR) significantly simplifies the process of prevention and treatment of patients compared with separate combination therapy by the oral drug+the parenteral drug.

In addition, the use of the new APC and the new parenteral drug of the present application provides, thanks to their inhibitor of replication (NIMR) of SARS-CoV-2 in the cell and inhibitor of entry (APR) of SARS-CoV-2 into the cell, have increased anti-SARS-CoV-2 activity.

In addition, the use of the new APC and the new parenteral drug of the present application provides, thanks to APR, a reduction in inflammation and thrombus formation in the moderate and severe COVID-19 patients.

Another aspect of the present application is directed to a method of obtaining the APC or the parenteral drug of the present application by dissolving NIMR, APR and excipients in saline (0.9% aqueous sodium chloride solution).

Another aspect of the present application is directed to a method of obtaining the APC or the new parenteral drug of the present application by dissolving a lyophilizate containing NIMR, APR and excipients in saline.

The active ingredients and the APC of the present application retain their activity in a convenient lyophilized form for storage.

Another aspect of the present application is directed to the use of APR in the form of a powder or a lyophilizate, or a concentrate, or a drug selected from the group consisting of TRASYLOL®, GORDOX®, APROTEX®, and TRASKOLAN® for preparing the APC or the parenteral drug of the present application.

Another aspect of the present application is directed to the use of NIMR in the form of a powder, or a lyophilizate, or a concentrate for preparing the PPC or the parenteral drug of the present application.

Another aspect of the present application is directed to the use of NIMR in the form of a powder, or a lyophilizate, or a concentrate and APR as TRASYLOL®, or GORDOX®, or APROTEX®, or ANTAGOSAN®, or CONTRYCAL®, or TRASKOLAN®, and others, for preparing the PPC or the parenteral drug of the present application.

Another aspect of the present application is a method for preparing the anti-SARS-CoV-2/COVID-19 pharmaceutical composition in form of PCL by dissolving APR, NIMR in the form of a powder, or a lyophilizate, or the water solution, and excipients in water or saline followed by lyophilization of the resulting mixture.

Another aspect of the present application is a method for preparing the PCL by dissolving NIMR in the form of a powder, or a lyophilizate, or the water solution, and excipients in TRASYLOL®, or GORDOX®, or APROTEX®, or ANTAGOSAN®, or CONTRYCAL®, or TRASKOLAN®, and others, followed by lyophilization of the resulting mixture.

The PPC can be obtained, including immediately before use, by sequential dissolution in physiological solution of the crystalline APR or its lyophilizate, the crystalline NIMR or its lyophilizate and, if necessary, excipients.

The APS can be obtained, including immediately before use, by dissolving the crystalline NIMR or its lyophilizate in an aqueous solution of APR or in known drugs that are aqueous solutions of APR, for example, Trasylol®, Gordox®, Aprotex®, or Traskolan®, and, if necessary, bringing the resulting compositions to the required concentration of active ingredients with saline.

The APC can be obtained, including immediately before use, by dissolution of BEXOVID in an aqueous solution of APR.

The APC can be obtained, including immediately before use, by dissolution of BEXOVID in the known drugs that are aqueous solutions of APR, for example, TRASYLOL®, or GORDOX®, or APROTEX®, or ANTAGOSAN®, or CONTRYCAL®, or TRASKOLAN®, and others, and, if necessary, bringing the resulting compositions to the required concentration of active ingredients with saline.

The new PPC can be obtained, including immediately before use, by sequential dissolution in saline of crystalline APR or its lyophilizate, for example, Contrykal®, the crystalline NIMR or its lyophilizate and, if necessary, excipients.

During intraperitoneal treating the transgenic mice (B6.Cg-Tg(K18-ACE2)2Prlmn/HEMI Hemizygous for Tg(K18-CE2)2Prlmn from Jackson Immuno-research, West Grove, Pa., USA; females, age—6-8 weeks, weighing 19-24 g) infected with mouse-adapted SARS-CoV-2 ("Dubrovka" strain, identification number GenBank: MW161041.1) a statistically significant reduction in virus titer by 4.2-4.6 orders of magnitude was obtained in the lungs of infected animals, compared with the control group of infected but untreated animals.

During intravenous treating the Syrian hamsters weighing 100-120 g (State Scientific Center for Virology and Biotechnology "Vector" of Rospotrebnadzor, Russia) infected with SARS-CoV-2 (strain hCoV-19/Australia/VIC01/2020), a statistically significant reduction in virus titer by order of magnitude was obtained in the lungs of infected animals, compared with the control group of infected but untreated animals.

Below are examples of the preparation and use of an anti-RNA viral preparation (anti-RNA viral pharmaceutical composition), confirming but not limiting the present application.

Example 1. Preparation of the Anti-SARS-CoV-2/COVID-19 Pharmaceutical Composition (APC-1-APC-3, PCL-2).

APC-1. NIMR from Shanghai XingMo Biotechnology Co., Ltd., China (20.0 mg), and APR from Wanhua Biochem, China (37.0 mg, 200,000 KIU), with an activity of 5400 KIU mg were dissolved in saline (20 ml) under ultrasonic stirring for 5 minutes to yield 20 ml APC-1 containing NIMR (1.0 mg/ml) and APR (10,000) KIU/ml.

APC-2 and PCL-2. 200.0 mg of NIMR from Shanghai XingMo Biotechnology Co., Ltd., China were dissolved in 10 ml GORDOX under ultrasonic stirring for 5 minutes to yield 10 ml APC-2 containing 20.0 mg/ml of NIMR and 10,000 KIU/ml of APR. The resulting APC-2 was lyophilized to give PCL-2 containing 200 mg NIMR and 100,000 KIU APR.

APC-3. 100.0 mg of NIMR from Shanghai XingMo Biotechnology Co., Ltd., China were dissolved in 10 ml GORDOX+90 ml saline under ultrasonic stirring for 5 minutes to yield 100 ml APC-3 containing 1.0 mg/ml of NIMR and 1,000 KIU/ml of APR.

Example 2. Stability of APC-1. The stability of APC-1 was studied by UV spectroscopy on an Agilent 8453 spectrophotometer after storage under normal conditions (1) and under stress tests (after exposure for 24 hours in the light at 25° C. (2); after exposure for 48 hours in the dark at 3-5° C. (3); after exposure for 48 hours in the dark at 25° C. (4); and after exposure for 48 hours in the dark at 60° C. (5)). The optical densities of the maxima of the initial spectra (condition 1) APC-1 differ greatly from those in the stress test. The percentage of change in optical density under conditions 3-5 compared to optical density under Conditions 1 is >2%. This indicates that APC-1 and APC-2 from are limitedly stable under rapid tests conditions and them must be used within a few hours after preparation.

Example 3. A device for inhalation therapy and prevention of SARS-CoV-2/COVID-19. 5-10 ml of APC-3 containing NIMR (1 mg/ml) and APR (1,000 KIU/ml) is placed into a compression nebulizer Omron NE-C300 Complete or in a portable ultrasonic Feellife Aerogo mesh nebulizer and is receive the device for inhalation therapy and prevention of SARS-CoV-2/COVID-19.

Example 4. Devices for nasal spray therapy and prevention of SARS-CoV-2/COVID-19. 5-10 ml of APC 3 containing NIMR (1 mg/ml) and APR (1000 KIU/ml) is placed into a plastic can for nasal and is receive the device for nasal therapy and prevention of SARS-CoV-2/COVID-19.

Example 5. Treatment with APC-2 of Transgenic Mice Infected with Mouse-Adapted SARS-CoV-2.

In the experiment, 4 groups of transgenic mice (B6.Cg-Tg(K18-ACE2)2Prlmn/HEMI Hemizygous for Tg(K18-CE2)2Prlmn from Jackson Immuno-research, West Grove, Pa., USA), females, age—6-8 weeks, weighing 19-24 g, were formed, 4 animals per group.

Group 1—control group, untreated mice: on day 1 in the morning the mice were infected with SARS-CoV-2, and then 5 ml/kg of water for injection was intragastrical administered immediately after infection and in the evening of the same day.

Group 2—treatment with GORDOX®—10 000 KIU/ml of APR. Dose: 50 000 KIU/kg APR.

Groups 3—treatment with saline solution of NIMR—20 mg/ml. Dose: 100.0 mg/kg of NIMR.

Groups 4—treatment with the APC-2. Dose: 50 000 KIU/kg of APR+100 mg/kg of NIMR.

Treatment regimen for transgenic mice: parenteral (intraperitoneal) administration of drugs 2 times a day; day 0-1 hour before infected with mouse-adapted SARS-CoV-2 ("Dubrovka" strain, identification number GenBank: MW161041.1) and 6-8 hours after infection; days 1, 2, 3-2 times a day, for a total of 4 days (days 0, 1, 2, 3); Day 4—lung sampling from all animals to assess the virus titer in the lungs, visual assessment of the lungs and transfer of the lungs for histology; days 0-4—daily assessment of body weight and condition of mice.

On day 0, animals from all groups were infected with the SARS-CoV-2 "Dubrovka" virus ($10^{3.5}$ $TCID_{50}$/ml). All mice were infected intranasally under light ether anesthesia in a volume of 30 μl for both nostrils.

Euthanasia (painless killing of the animal) was carried out by the responsible person in accordance with the existing ethical requirements, by dislocation of the cervical vertebrae with preliminary anesthesia with ether. Euthanasia was performed promptly after the end of the experiments.

On day 4 post-infection with the virus, the animals in each group were sacrificed and the lungs were removed under sterile conditions. One lung was fixed in formalin for further histology, the second lung was prepared to measure the virus titer. To do this, after washing three times in a solution of 0.01 M phosphate buffered saline (PBS), the lungs were homogenized and resuspended in 1 ml of cold sterile PBS. The suspension was cleared from cell debris by centrifugation at 2000 g for 10 min, and the supernatant was used to determine the infectious titer of the virus in cell culture and to perform PCR. The obtained samples were stored at −80° C. until the experiments were carried out.

To determine the infectious titer of the virus from the lungs of mice, Vero CCL81 cells were seeded in 96-well Costar plates with an average density of 20,000 cells per well and grown in DMEM medium in the presence of 5% fetal calf serum, 10 mM glutamine and antibiotics (penicillin 100 IU/well). ml and streptomycin 100 μg/ml) until a complete monolayer is formed (within 3 days). Before infection with the virus, the cell culture was washed twice with DMEM medium without serum. 10-fold dilutions of each lung virus sample were prepared from 10-1 to 10-7. The prepared dilutions in a volume of 200 μL were added to cell culture plates and incubated in 5% CO2 at 37° C. for 5 days until a cytopathic effect (CPE) appeared in virus control cells. Accounting for the result of the manifestation of CPP in cells was carried out using a quantitative MTT test. The virus titer was calculated using the Ramakrishnan M.A formula in the Excel program [M.A. Ramakrishnan. Determination of 50% endpoint titer using a simple formula. *World J. Virol.* 2016, 5, 85-86. doi: 10.5501/wjv.v5.i2.85] and expressed as lg$TCID_{50}$/ml ($TCID_{50}$—The median tissue culture infectious dose is defined as the dilution of a virus required to infect 50% of a given cell culture.) [I. Leneva et al. Antiviral Activity of Umifenovir In Vitro against a Broad Spectrum of Coronaviruses, Including the Novel SARS-CoV-2 Virus. Viruses 2021, 13(8): 1665. doi: 10.3390/v13081665]. Next, the average titer value for samples from mice of the same group was calculated.

The effectiveness of the drugs in a model of the transgenic mice infected with mouse-adapted SARS-CoV-2 was assessed according to decrease in the titer of the virus in the lungs of animals after 4 days.

The obtained digital data were subjected to statistical processing in the "Statistica 8.0" software. The results are shown in Table 2.

TABLE 2

The effectiveness of the drugs and control (unreated mice) on the model the transgenic mice infected with mouse-adapted SARS-CoV-2.

| Group | Dose of drug | log$TCID_{50}$/ml | [a]Decrease in logTCID50/mL |
|---|---|---|---|
| 1 | Control | 8, 83; 9, 50; 8, 17; 8, 5; 8, 83 (8, 77) | — |
| 2 | 50000 KIU/kg APR | 7, 17; 6, 50; 8, 17; 7, 17 (7, 25) | 1.52 |
| 3 | 100 mg/kg NIMR | 6.17, 6.83, 6.83, 5.83 (6.42) | 2.35 |
| 4 | APC-2 (100 mg/kg NIMR + 50000 KIU/kg APR) | 5.17, 5.50, 5.50, 5.50, 6.17 (5, 57) | 3.20 |

[b]% reduction in virus titer (log$TCID_{50}$/ml) compared to control (group 1).

As can be seen from Table 2, parenteral (intraperitoneal) treatment of mice infected with SARS-CoV-2 resulted in a reduction in virus titer in the lungs of infected animals compared to a control group of infected but untreated animals. Thus, with parenteral monotherapy with APR or NIMR, a decrease in virus titer (log$TCID_{50}$/ml) by 1.52 and 2.35, respectively, was observed. At the same time, combination parenteral therapy of APR+MOV provides a decrease in virus titer by 3.2 orders of magnitude.

Example 6. Intravenous Treatment of Syrian Hamsters Infected with the SARS-CoV-2 Using the APC-2 Containing NIMR and APR.

The efficacy of the APC-2 of the present application was evaluated using a model of SARS-CoV-2 infection in Syrian hamsters [R. Boudewijns et al. STAT2 signaling as double-edged sword restricting viral dissemination but driving severe pneumonia in SARS-CoV-2 infected hamsters. BioRxiv preprint. doi: https://doi.org/10.1101/

2020.04.23.056838; this version posted Apr. 24, 2020. https://www.biorxiv.org/content/10.1101/2020.04.23.056838v1].

The strain SARS-CoV-2 hCoV-19/Australia/VIC01/2020 was obtained from the State Research Center of Virology and Biotechnology VECTOR (Russia). The infectious virus was isolated by sequential passage in Vero E6 cells. The titer of the viral suspension was determined by endpoint dilution on Vero E6 cells using the Reed-Muench method. The work related to the live virus was carried out under isolated laboratory conditions that meet the international BSL-3+ VECTOR requirements.

Vero E6 cells from VECTOR's Collection of Cell Cultures were cultured in Minimum Essential Medium (MEM) (Gibco) supplemented with 10% fetal bovine serum (Integro), 1% L-glutamine (Gibco), and 1% Bicarbonate (Gibco). Endpoint titrations were performed with a medium containing 2% fetal bovine serum.

Wild-type Syrian hamsters at the age of 6-10 months weighing 100-120 g from State Scientific Center for Virology and Biotechnology "Vector" of Rospotrebnadzor (Russia) were kept with unlimited access to food and water. Hamsters were randomized into 4 cohorts, 8 animals in each cohort (4 males and 4 females).

Hamsters were anesthetized with zoletil-xyla and inoculated into each nostril with 50 µl anesthetic combination containing $10^3 TCID_{50}$.

Group 1—control group, untreated hamsters. Dose: 5 ml/kg saline.

Group 2—treatment with GORDOX®—10 000 KIU/ml of APR. Dose: 10000 KIU/kg APR.

Groups 3—treatment with saline solution of NIMR—20 mg/ml. Dose: 100.0 mg/kg of NIMR.

Groups 4—treatment with the APC-2 (NIMR—20 mg/ml+10000 KIU/ml of APR). Dose: 50 000 KIU/kg of APR+100 mg/kg of NIMR.

The drugs were injected under light isoflurane anesthesia intravenously, 2 times a day for 4 days, starting the first injection one hour before infection, 6 hours after infection, then for 3 days after 12 hours.

Hamsters were checked daily for appearance, behavior and weight. On the 4th day after infection, the hamsters were euthanized by intravenous injection of 500 µl doletal (200 mg/ml sodium pentobarbital, V6toquinol SA). Hamster lung tissues were harvested after sacrifice and homogenized using a Precellys homogenizer in a 350 µl RNeasy lysis buffer (RNeasy Mini kit, Qiagen) and centrifuged (10,000 rpm, 5 min) to remove cell debris. RNA was extracted according to the manufacturer's instructions. Real-time PCR was performed on the LightCycler96 platform (Roche) using the iTaq Universal Probes One-Step RT-qPCR kit (BioRad) [R. Boudewijns et al. STAT2 signaling as double-edged sword restricting viral dissemination but driving severe pneumonia in SARS-CoV-2 infected hamsters. BioRxiv preprint. doi: https://doi.org/10.1101/2020.04.23.056838; this version posted Apr. 24, 2020. https://www.biorxiv.org/content/10.1101/2020.04.23.056838v1].

For histological analysis, lung tissue was fixed in 4% formaldehyde, embedded in paraffin, and stained with hematoxylin-eosin. Damage was assessed on a scale from 1 to 3: stagnation, intra-alveolar bleeding, apoptotic bodies in the bronchial epithelium, necrotic bronchiolitis, perivascular edema, bronchopneumonia, perivascular inflammation, peribronchial inflammation, and vascular inflammation.

Statistical analysis was performed using the GraphPed Prism software from GraphPed Software, Inc. Statistical significance was determined using the Mann-Whitney non-parametric U-test. The values of $P<0.05$ were considered significant.

An analysis of the results obtained showed that APC-2 comprising NIMR and APR demonstrated a high anti-SARS-CoV-2/COVID-19 efficacy. Thus, in comparison with the control group, after intravenous treatment of Syrian hamsters infected with the SARS-CoV-2 of drug APC-2, the titer of SARS CoV-2 in the tissues of the lungs decreased by more than an order of magnitude compared to the control group.

The invention claimed is:

1. A combination therapy or prevention of SARS-CoV-2 infection or a disease associated with SARS-CoV-2 infection, comprising:
    administration to the patient of a therapeutically effective amount of aprotinin and nirmatrelvir.

2. The combination therapy and prevention of claim 1, comprising:
    an additional administration to the patient of a therapeutically effective amount of ritonavir.

3. The combination therapy or prevention of claim 1, wherein the disease associated with SARS-CoV-2 is COVID-19.

4. The combination therapy or prevention of claim 1, wherein aprotinin is a pharmaceutical composition containing an aprotinin in a dissolved form.

5. The combination therapy or prevention of claim 1, wherein nirmatrelvir is a pharmaceutical composition containing nirmatrelvir.

6. The combination therapy or prevention of claim 1 comprising:
    administering parenterally to a mammal aprotinin and nirmatrelvir.

7. The combination therapy or prevention of claim 6, comprising:
    wherein a parenteral administration is intravenous, inhalation, or nasal administration.

8. A pharmaceutical composition in the form of an aqueous solution or a lyophilizate for the treatment or prevention of a SARS-CoV-2 infection or a disease associated with SARS-CoV-2 infection, comprising:
    a therapeutically effective amount of aprotinin, nirmatrelvir and pharmaceutically acceptable salts thereof, and excipient.

9. The combination therapy or prevention of claim 1, wherein the aprotinin and nirmatrelvir are administered separately or as a combined pharmaceutical for parenteral administration.

10. The combination therapy or prevention of claim 3, wherein the aprotinin and nirmatrelvir are administered separately or as a combined pharmaceutical for parenteral administration.

11. The combination therapy or prevention of claim 5, wherein the aprotinin and nirmatrelvir are administered separately or as a combined pharmaceutical for parenteral administration.

12. The combination therapy or prevention of claim 6, wherein the aprotinin and nirmatrelvir are administered separately or as a combined pharmaceutical for parenteral administration.

13. The combination therapy or prevention of claim 7, wherein the aprotinin and nirmatrelvir are administered separately or as a combined pharmaceutical for parenteral administration.

* * * * *